United States Patent [19]

Kroll et al.

[11] Patent Number: 5,531,766
[45] Date of Patent: Jul. 2, 1996

[54] IMPLANTABLE CARDIOVERTER DEFIBRILLATOR PULSE GENERATOR KITE-TAIL ELECTRODE SYSTEM

[75] Inventors: Mark W. Kroll, Minnetonka; Randall S. Nelson, Pine Springs; Theodore P. Adams, Edina, all of Minn.

[73] Assignee: Angeion Corporation, Plymouth, Minn.

[21] Appl. No.: 376,806

[22] Filed: Jan. 23, 1995

[51] Int. Cl.⁶ .................................................. A61N 1/39
[52] U.S. Cl. .............................. 607/5; 607/9; 607/36
[58] Field of Search ............................. 607/5, 9, 10, 71, 607/36, 119; 128/695, 696, 700

[56] References Cited

U.S. PATENT DOCUMENTS

| | | |
|---|---|---|
| 3,478,746 | 11/1969 | Greatbatch .................................. 607/9 |
| 3,735,766 | 5/1973 | Bowers et al. ............................ 607/36 |
| 3,920,888 | 11/1975 | Barr ........................................... 607/36 |
| 4,549,548 | 10/1985 | Wittkampf et al. ....................... 607/36 |
| 5,235,978 | 8/1993 | Hirschburg et al. ........................ 607/5 |
| 5,241,960 | 9/1993 | Anderson et al. .......................... 607/5 |
| 5,376,103 | 12/1994 | Anderson et al. .......................... 607/5 |
| 5,405,363 | 4/1995 | Kroll et al. ................................. 607/5 |

Primary Examiner—Angela D. Sykes
Assistant Examiner—Stephen Huang
Attorney, Agent, or Firm—Patterson & Keough

[57] ABSTRACT

An electrode system for an implantable cardioverter defibrillator. The electrode system includes a conductive structure which is physically and electrically connected to the housing or can of the implantable cardioverter defibrillator and is used as an electrode in combination with an existing implantable cardioverter defibrillator electrode or electrodes. The electrode system provides a therapeutically significant increase in the effective surface area of the implantable cardioverter defibrillator's electrodes without requiring an additional header connection, feedthru, or cable.

12 Claims, 4 Drawing Sheets

IMPLANTABLE CARDIOVERTER DEFIBRILLATOR PULSE GENERATOR KITE-TAIL ELECTRODE SYSTEM

BACKGROUND OF THE INVENTION

1. Field of the Invention

This invention relates to medical devices, and more particularly to implantable cardioverter defibrillators (ICD) used to cardiovert and/or defibrillate a human being. The ICD pulse generator kite-tail electrode system of this invention improves the performance of ICDs.

2. Background Information

The implantable cardioverter defibrillator is a well established therapy for malignant ventricular arrhythmia. The ICD senses an arrhythmia, stores a charge in an internal capacitor, and delivers that charge to the heart through electrodes.

An early form of electrodes are epicardial or pericardial patches which are sewn to the surface of the heart. Electrodes of this type are shown in FIG. 1. Epicardial or pericardial patch electrodes are disclosed in U.S. Pat. No. 4,821,723 to Baker, Jr. et al. and U.S. Pat. No. 4,827,932 to Ideker, et al. Another well know form of electrodes are endocardial lead electrodes which traverse the patient's vasculature and are disposed within the heart, preferably the right ventricle. A hybrid system uses endocardial leads in conjunction with epicardial patches. This system is disclosed in U.S. Pat. No. 4,548,203 to Tacker, Jr. et al. and U.S. Pat. No. 4,641,656 to Smits.

Most electrode systems which utilize epicardial patches require open chest surgery for implantation and positioning. Such surgery is traumatic, risky, expensive and requires a long patient recovery period. Referring to FIG. 2, procedures were therefore developed to subcutaneously implant a patch electrode in the left side of the patents chest or in the back under the shoulder blade. U.S. Pat. No. 4,662,377 to Hileman et al. teaches such a method. U.S. Pat. No. 4,727,877 to Kallock and U.S. Pat. No. 5,014,696 to Mehra disclose a similar method wherein a rigid plate is used in place of a patch. The advantage of these subcutaneous implantation methods is that major surgery is avoided, while at the same time improved performance is provided by the combination of the large surface area electrode element with the endocardial lead electrode.

Another approach used is to pericardially implant an electrode. In such systems, an electrode is implanted near the epicardial surface of the heart via an insertion through a small incision or an introducer apparatus. The electrodes simulate the epicardial electrodes, but avoid the trauma of open chest surgery. Pericardial electrodes and methods are disclosed in U.S. Pat. No. 4,860,769 to Fogarty et al. and U.S. Pat. No. 4,991,578 to Cohen.

Referring to FIG. 3, a recent development in ICD electrodes is the "pitchfork electrode" disclosed in U.S. Pat. No. 5,203,348 to Dahl, et al. This approach replaces the large surface area of the subcutaneous patch style electrode comprising three parallel wires forced about the patient's left side. Although the surface area of the electrodes is not great, the convex hull "outline" or "shadow" formed by the wires is large. This technique results in a very low impedance and also low defibrillation energy thresholds. Unfortunately, the implantation technique is complex and time consuming. Also, the low impedance is not consistent with the modern trend toward smaller ICD capacitance's which show the most benefit with high impedance.

Referring to FIG. 4, another recent electrode system approach is to use the housing or can of the ICD pulse generator as an electrode in conjunction with an endocardial lead electrode. This technique is shown in published European Patent Application 0453761A1 and in U.S. Pat. No. 5,133,353 to Hauser, U.S. Pat. No. 5,261,400 to Bardy and in U.S. Pat. No. 5,376,103 to Anderson. This approach, although it has advantages, is inconsistent with another trend in ICD design, namely that toward smaller ICD housing. Smaller housings will reduce the effective size of the electrode formed thereby, which will yield reduced performance. Anderson teaches the use of a subcutaneous electrode in conjunction with the ICD housing electrode, but this technique requires the addition of an external connection to the housing and the attendant complication of connectors, feedthrus, and cables, as well as the resultant increase in size of the housing, to accommodate the connector and feedthru.

Despite the need in the art for a safe, easy to implant, effective, and reliable electrode system for use with an ICD, and which overcomes the disadvantages, shortcomings and limitations of the prior art, none insofar as is known has been developed or proposed.

Accordingly, it is an object of the present invention to provide a new electrode system for use with an ICD. It is a further object of this invention to provide an electrode system which is safe, easy to implant, reliable and effective, and which overcomes the limitations and shortcomings of the prior art.

SUMMARY OF THE INVENTION

The present invention provides an electrode system for an implantable cardioverter defibrillator, including a conductive structure which is physically and electrically connected to the housing or can of the implantable cardioverter defibrillator and is used as an electrode in combination with an existing implantable cardioverter defibrillator electrode or electrodes. The electrode system provides a significant increase in the effective surface area of the implantable cardioverter defibrillator's electrodes.

In a basic aspect, the invention includes an implantable cardioverter defibrillator pulse generator including a housing having an exterior surface, an interior surface defining a sealed interior space containing pulse generation circuitry, and means, disposed on the exterior surface, to connect an external electrode to the pulse generation circuitry, wherein the improvement comprises, a conductive tail electrode physically connected to the exterior surface of the housing, the tail electrode having a predetermined surface area.

In a preferred embodiment, the invention yields a pulse generator for use in an implantable cardioverter defibrillator system having at least one externally connected electrode, comprising:

(a) pulse generation circuitry;

(b) a housing having an exterior surface, an interior surface defining a sealed interior space containing the pulse generation circuitry, and means, disposed on the exterior surface, to connect an external electrode to the pulse generation circuitry, the housing exterior surface comprising a conductive, metallic portion which is electrically connected to the pulse generation circuitry;

(c) a metallic, conductive connection tube connected to the housing; and (d) an elongated, flexible conductive tail electrode of a predetermined length connected to the exterior surface of the housing via the connection robe, the tail electrode having a first predetermined surface area, the tail electrode further being electrically connected to the housing exterior surface, whereby the housing exterior surface and the tail electrode cooperate to yield a composite electrode surface area of a second, greater, predetermined surface area.

The features, benefits and objects of this invention will become clear to those skilled in the art by reference to the following description, claims and drawings.

DESCRIPTION OF THE PREFERRED EMBODIMENTS

The implantable cardioverter defibrillator is an important tool for managing the health of patients who have a history of heart problems. The ICD effects defibrillation of the human heart by passing a current through the heart for a predetermined time period. A voltage is generated in the ICD pulse generator and transmitted to the heart through electrodes. To successfully defibrillate an exemplary heart with a given set of electrodes, a current of approximately 6–11.5 A is required to produce a pulse width of 13–2 ms., respectively.

Figure 1:
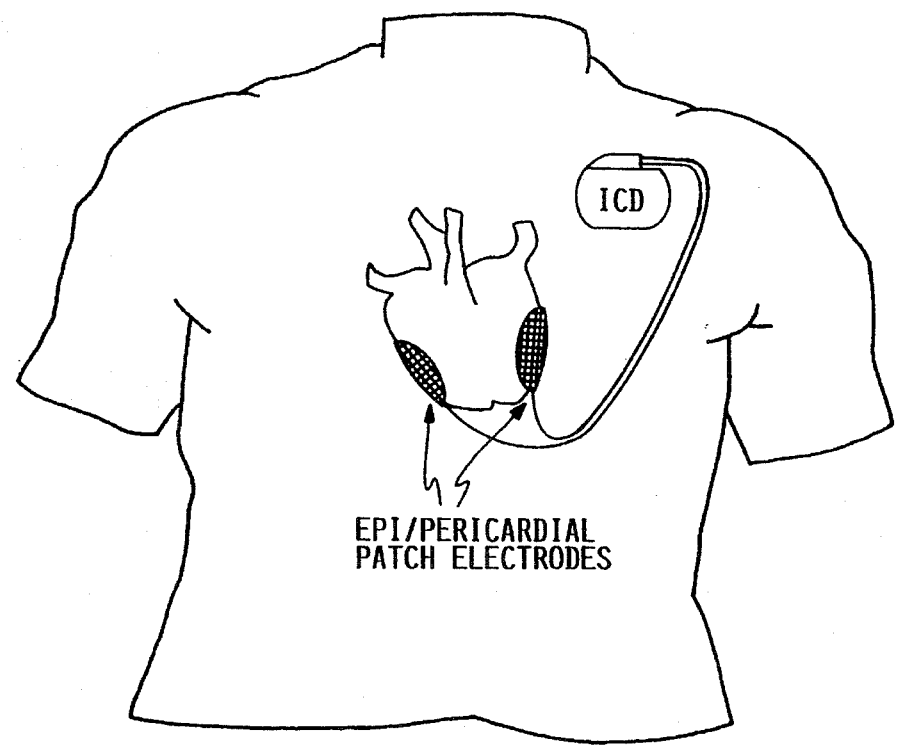
FIG. 1 illustrates the prior art ICD electrode system having at least one epicardial patch electrode attached directly to the heart.
Figure 2:
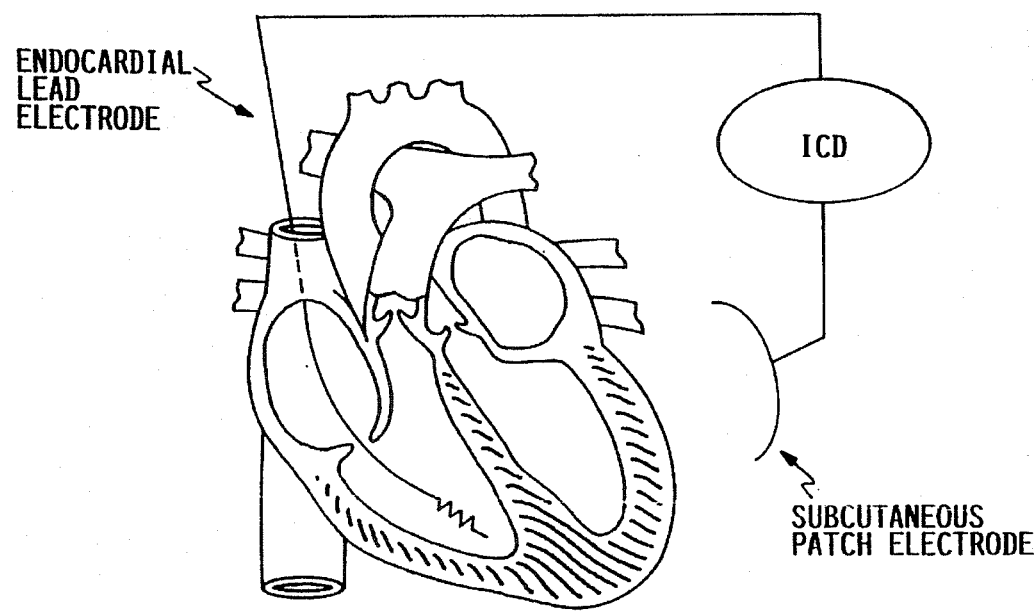
FIG. 2 illustrates the prior art ICD electrode system having an epicardial patch electrode and an endocardial lead electrode disposed within a chamber of the heart.
Figure 3:
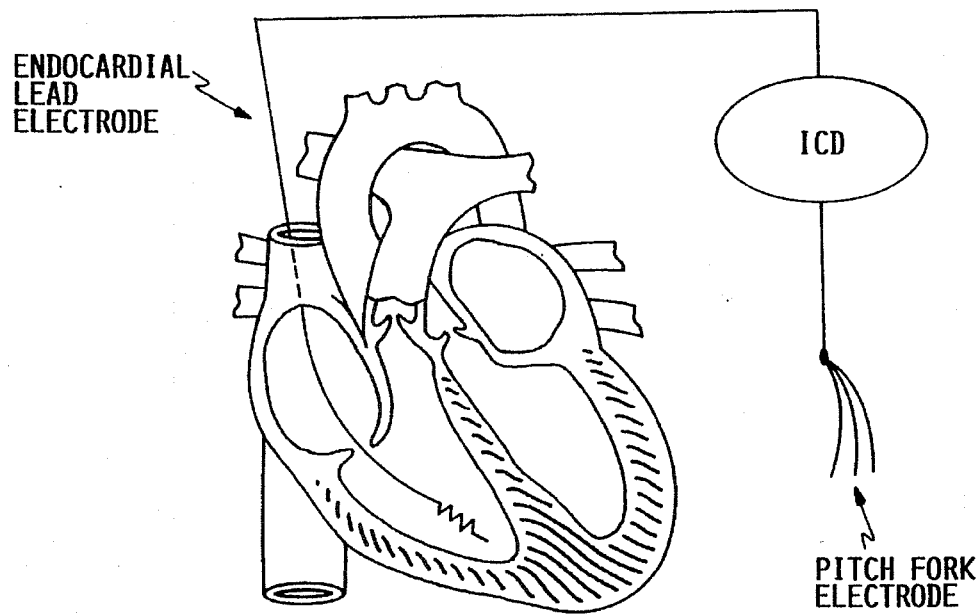
FIG. 3 illustrates the prior art ICD electrode system having a subcutaneously implanted "pitchfork" style electrode in combination with an endocardial lead electrode.
Figure 4:
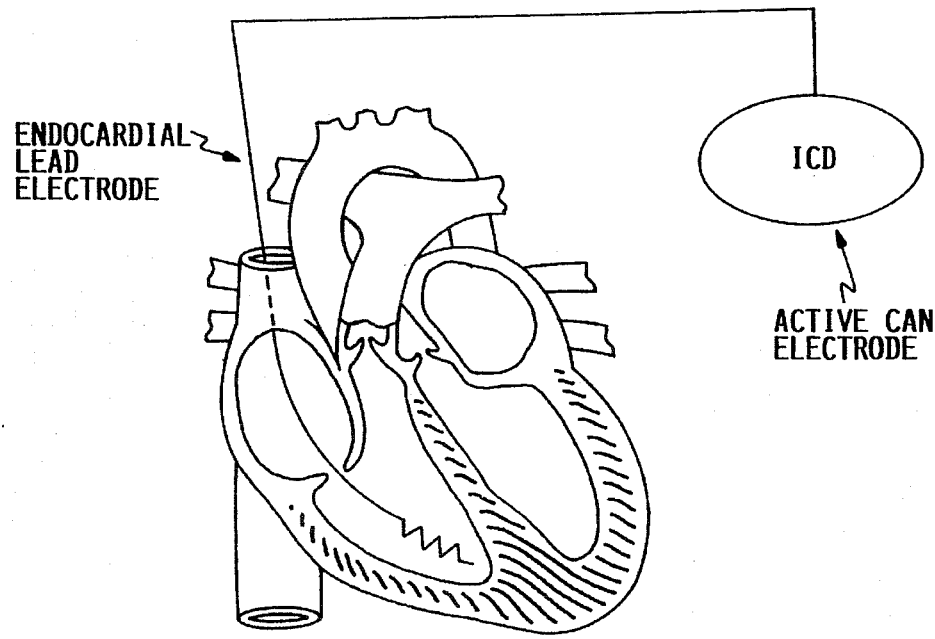
FIG. 4 illustrates the prior art ICD electrode system wherein the housing of the ICD pulse generator is utilized as an electrode in combination with an endocardial lead electrode.
Figure 5:
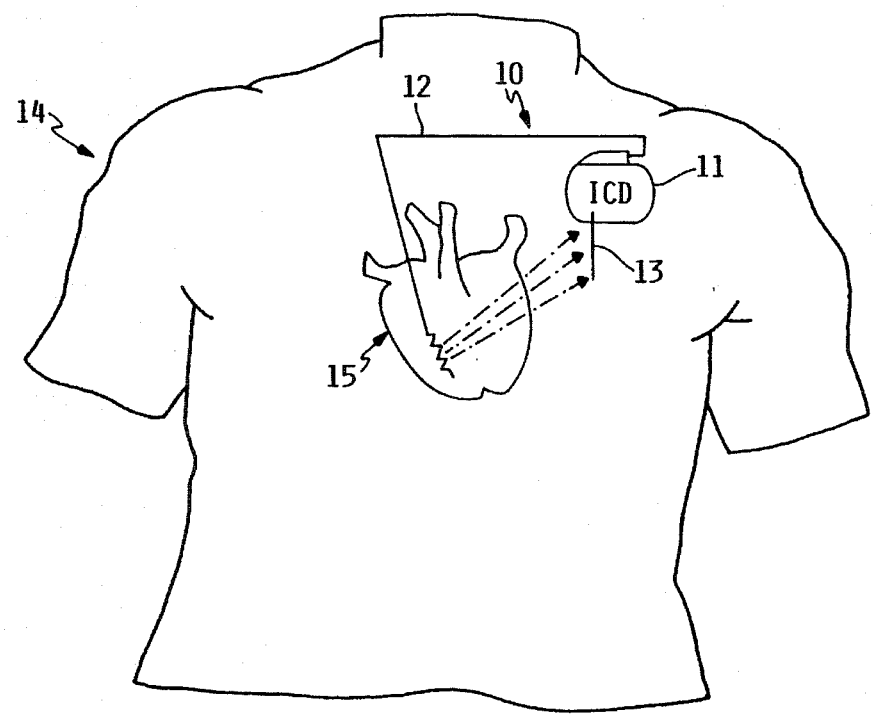
FIG. 5 illustrates the ICD electrode system of the present invention, one embodiment of which comprises a kite-tail member attached to a pulse generator and working in combination with an endocardial lead electrode.

The present invention provides an electrode system for an implantable cardioverter defibrillator. Referring to FIG. 5, the ICD electrode system 10 of the present invention basically comprises an implantable pulse generator 11, an endocardial lead 12 connected to the pulse generator 11 via connection ports, and a kite-tail electrode 13 connected directly to the housing of the pulse generator 11.

The ICD pulse generator 11 is a sealed, canister-like unit which is implanted in the patient's body 14 and contains various electronic components. Implantation is made subcutaneously in the left chest area of the patient 14. The internal components (not shown) of the pulse generator 11 comprise a battery, charge storage means, preferably one or more capacitors, connected to the battery, electrode connection means connectable to the charge storage means and connected to the electrodes when in an operative orientation, and switch means connected to the charge storage means and to the electrode connection means for controlling the delivery of a high voltage defibrillation pulse, of a predetermined polarity, to the patient 14. The aforementioned internally disposed electrical components are well known in the art.

The endocardial lead electrode 12 is of a design which is known in the art. The electrode 12 extends from the implanted pulse generator canister 11 through the vascular system of the patient 14 to the heart 15. The endocardial lead electrode 12 preferably comprises at least two metallic or semi-metallic electrode members which are disposed in the chamber(s) of the heart 15. The electrode members typically are formed of coiled metal bands. Each electrode member is connected to an elongated conductive lead or wire. The leads are encased in a non-conductive sheath. The leads terminate in connectors which are attached to the pulse generator 11.

Figure 6:
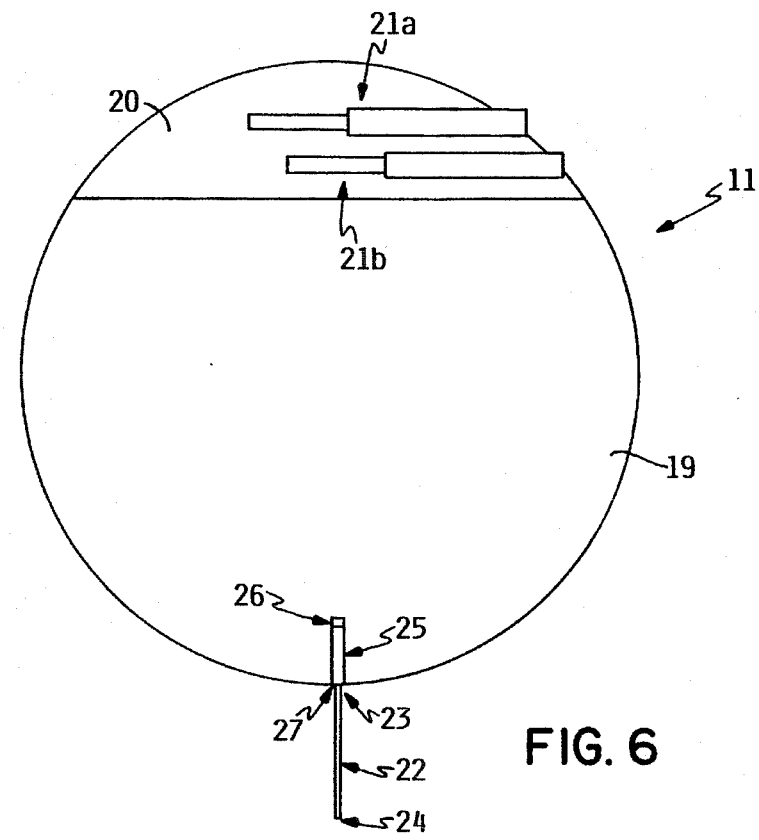
FIG. 6 is a plan view of an embodiment of the ICD electrode system of this invention.

FIG. 6 shows a preferred embodiment of the pulse generator 11. The pulse generator 11 has a housing or can 19 which has a hollow interior for containing the aforementioned electrical components. The housing 19 may be oval, rectangular or irregularly shaped and is constructed of a non-reactive metal, preferably titanium. A header 20, preferably constructed of a polymeric material or non-reactive metal, is sealingly disposed at the top of the housing 19. The header 20 has a pair of electrode connectors 21 a and b. The electrode connectors 21 a and b are connectable, as is known in the art, to the endocardial lead electrode connectors located at the terminal end of the endocardial lead electrode leads. The connectors 21 a and b are connected to conductive leads which extend through apertures (not shown) in the header 21 into the interior of the pulse generator 11, where they are communicatively connected to the circuit components thereof The apertures are designed with known feedthru structures which seal and isolate the pulse generator 11 interior from the patient. Although the pulse generator 11 is preferably of the type wherein the metal housing 19 functions as an electrode in the ICD system 10, in conjunction with the endocardial electrode 12 or any other electrode or electrodes, it is within the purview of the invention that the housing not function as an electrode.

The kite tail electrode 22 is a thin, elongated structure of a predetermined length with proximal and distal ends 23 and 24, respectively. The tail electrode 22 has a length of 2–30 cm., and preferably 10–20 cm. The electrode 22 is constructed of metallic wire or cable, preferably composed of titanium, MP35N, stainless steel, or platinum. The overall diameter of the tail electrode 22 is 0.5–10 mm. A 1.0–5 mm diameters is preferred as a best compromise between compactness and strength.

Figure 7:
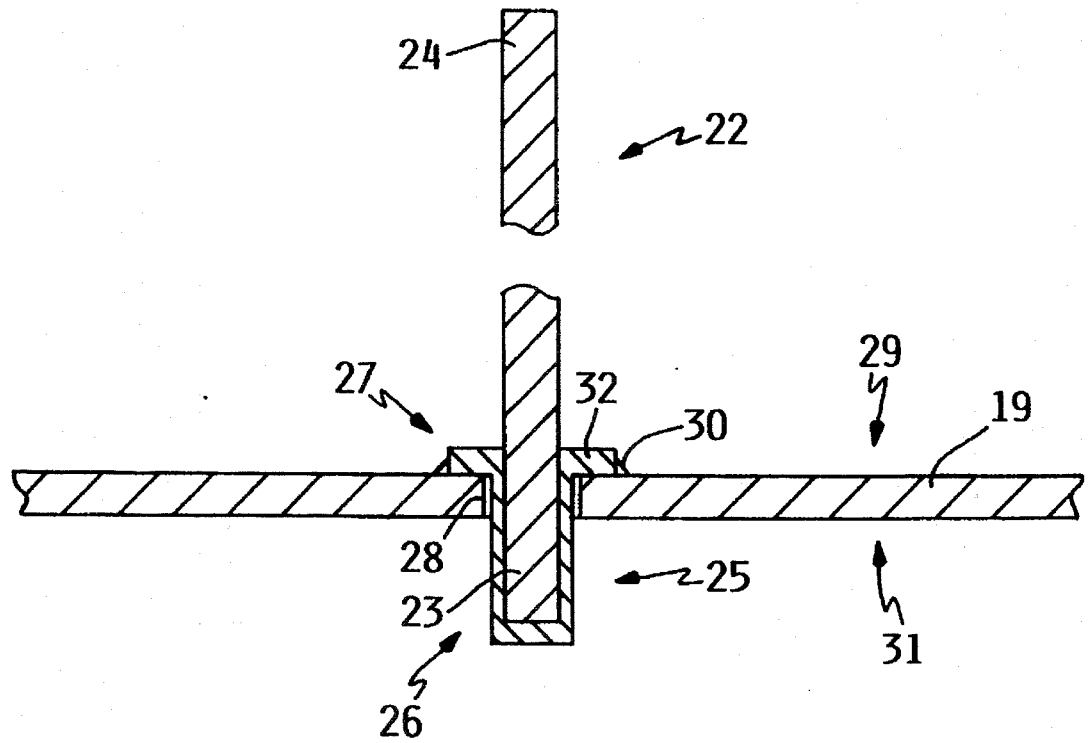
FIG. 7 is a detailed view of an embodiment of the ICD electrode system of this invention.

Referring also to FIG. 7, a connection tube 25 with one closed end 26 and an open end 27 with a circumferential, low profile flange 32 is disposed on the exterior surface 29 of the can 19. The connection tube 25 is preferably constructed of titanium and has an inside diameter and depth sufficient to allow insertion of the tail electrode 22 proximal end 23 therein. The closed end 26 of the flanged tube 25 is inserted and the flange 32 is welded 30 at an aperture 28 in the titanium can 19 at a predetermined point, for example the edge opposite the header 20.

The proximal end 23 of the electrode 22 is inserted into the open, flanged end 27 of the connection tube 25. The connection tube 25 is then crimped interiorly to hold the electrode 22 in place. The crimped tube connector structure 25 maintains the hermetic seal between inside 31 and outside 29 surfaces of the pulse generator 11. If removal of the electrode tail 22 is required, for any reason, it may easily be cut loose, or in the alternative, freed by a sharp tug on the electrode tail 22. Full withdrawal of the electrode tail 22 from the patient body 14 may then be easily accomplished. After withdrawal of the electrode tail 22, a smooth non-irritating surface remains on the can 19. Importantly, the hermeticity of the interior 31 of the pulse generator 11 is maintained without the use of additional feedthru mechanism.

In one alternative embodiment, the welded flange tube is reusable to allow the removal of the tail or substitution of various tail lengths. In another alternative embodiment, the distal end of the kite tail electrode 22 may additionally have either molded tines or a molded tie-down section to firmly fixate the distal end of the electrode. Such fixation prevents any wandering of the electrode from its inserted, tested position. In yet another alternative embodiment, the electrode tail can be inserted or extracted repeatedly. The device has a terminal block in the header that is tied to the housing of the pulse generator. Fixation of the electrode tail to the block is made via a set screw or a similar positive locking mechanism.

In summary, the kite-tail electrode 22 is a conductive structure which is physically and electrically connected to the exterior of the housing 19 of the pulse generator 11 of the implantable cardioverter defibrillator 10 and is used as an electrode in combination with the endocardial lead electrode 12 and/or other electrodes. This electrode 22 provides a significant increase in the overall effective electrode surface area of the ICD system 10. The increased electrode surface area is believed to be therapeutically significant. Importantly, the electrode of this invention utilizes a direct metallic and conductive extension of the can or housing, and hermeticity is maintained with no connection through the header assembly and associated feedthru devices.

As many changes are possible to the embodiments of this invention utilizing the teachings thereof, the descriptions above, and the accompanying drawings should be interpreted in the illustrative and not the limited sense.

The invention claimed is:

1. In an implantable cardioverter defibrillator pulse generator including a housing having an exterior surface, an interior surface defining a sealed interior space containing pulse generation circuitry, and means, disposed on said exterior surface, to connect an external electrode to said pulse generation circuitry, the combination with said cardioverter defibrillator pulse generator of a conductive tail electrode physically connected to said exterior surface of said housing, said tail electrode having a predetermined surface area, said tail electrode further having a length of 2–30 cm. and a diameter of 0.5–10 mm.

2. The implantable cardioverter defibrillator pulse generator of claim 1, wherein said housing exterior surface comprises a conductive, metallic portion which is electrically connected to the pulse generation circuitry, and wherein said tail electrode is electrically connected to said housing exterior surface, whereby said housing exterior surface and said tail electrode cooperate to yield a composite electrode surface area.

3. The implantable cardioverter defibrillator pulse generator of claim 2, wherein said housing exterior surface conductive portion is constructed of a material selected from the group of materials consisting of titanium, MP35N, stainless steel and platinum.

4. The implantable cardioverter defibrillator pulse generator of claim 2, further comprising means to connect said electrode tail to said housing exterior surface.

5. The implantable cardioverter defibrillator pulse generator of claim 4, wherein said means to connect said electrode tail to said housing exterior surface comprises a tube which is closed at one end and open at an opposite, flanged end, said tube being inserted in and welded to an aperture in said housing exterior surface, said tail electrode being inserted in said open, ranged end and said tube being crimped to retain said tail electrode therein.

6. The implantable cardioverter defibrillator pulse generator of claim 5, wherein said tube closed end is further disposed in an aperture in said housing exterior surface.

7. The implantable cardioverter defibrillator pulse generator of claim 1, wherein said tail electrode is constructed of metal wire selected from the group consisting of titanium, MP35N, stainless steel and platinum wires.

8. The implantable cardioverter defibrillator pulse generator of claim 1, wherein said tail electrode is constructed of metal cable selected from the group consisting of titanium, MP35N, stainless steel and platinum cables.

9. The implantable cardioverter defibrillator pulse generator of claim 1, wherein said tail electrode is an elongated, flexible structure.

10. The implantable cardioverter defibrillator pulse generator of claim 1, where said tail electrode has a length of 10–20 cm. and a diameter of 1.0–5.0 mm.

11. In an implantable cardioverter defibrillator pulse generator including a housing having an exterior surface, an interior surface defining a sealed interior space containing pulse generation circuitry, and means, disposed on said exterior surface, to connect an external electrode to said pulse generation circuitry, said housing exterior surface comprising a conductive, metallic portion which is electrically connected to the pulse generation circuitry, the combination with said cardioverter defibrillator pulse generator of a conductive tail electrode physically connected to said exterior surface of said housing, said tail electrode having a first predetermined surface area, said tail electrode further having a length of 2–30 cm. and a diameter of 0.5–10 mm., and said tail electrode being electrically connected to said housing exterior surface, whereby said housing exterior surface and said tail electrode cooperate to yield a composite electrode surface area of a second predetermined surface area.

12. A pulse generator for use in an implantable cardioverter defibrillator system having at least one externally connected electrode, comprising:

(a) pulse generation circuitry;

(b) a housing having an exterior surface, an interior surface defining a sealed interior space containing said pulse generation circuitry, and means, disposed on said exterior surface, to connect an external electrode to said pulse generation circuitry, said housing exterior surface comprising a conductive, metallic portion which is electrically connected to the pulse generation circuitry;

(c) a metallic, conductive connection tube welded to said housing; and (d) an elongated, flexible conductive tail electrode of a predetermined length connected to said exterior surface of said housing via said connection tube, said tail electrode having a first predetermined surface area, said tail electrode further having a length of 10–20 cm and a diameter of 1.0–5.0 mm., said tail electrode further being electrically connected to said housing exterior surface, whereby said housing exterior surface and said tail electrode cooperate to yield a composite electrode surface area of a second, greater, predetermined surface area.

\* \* \* \* \*